(12) United States Patent
Wilkinson

(10) Patent No.: US 6,562,592 B1
(45) Date of Patent: May 13, 2003

(54) POLYNUCLEOTIDE ENCODING ESTROGEN RECEPTOR

(75) Inventor: Hilary Wilkinson, Springfield, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/558,795

(22) Filed: Apr. 26, 2000

Related U.S. Application Data

(62) Division of application No. 09/139,617, filed on Aug. 25, 1998, now Pat. No. 6,222,015.
(60) Provisional application No. 60/060,520, filed on Sep. 30, 1997, and provisional application No. 60/058,271, filed on Sep. 8, 1997.

(51) Int. Cl.$^7$ ................................................. C12N 5/10
(52) U.S. Cl. .................... 435/69.1; 435/320.1; 435/325; 536/23.5
(58) Field of Search ............................ 435/69.1, 320.1, 435/325; 536/23.5

(56) References Cited

U.S. PATENT DOCUMENTS

| | | |
|---|---|---|
| 4,605,649 A | 8/1986 | Liehr |
| 5,071,773 A | 12/1991 | Evans et al. |
| 5,217,867 A | 6/1993 | Evans et al. |
| 5,262,300 A | 11/1993 | Evans et al. |
| 5,298,429 A | 3/1994 | Evans et al. |
| 5,310,662 A | 5/1994 | Evans et al. |
| 5,312,732 A | 5/1994 | Evans et al. |
| 5,438,126 A | 8/1995 | DeGroot et al. |
| 5,508,164 A | 4/1996 | Kausch et al. |
| 5,534,418 A | 7/1996 | Evans et al. |
| 5,597,693 A | 1/1997 | Evans et al. |
| 5,597,705 A | 1/1997 | Evans et al. |
| 5,599,904 A | 2/1997 | Evans et al. |
| 5,602,009 A | 2/1997 | Evans et al. |
| 5,639,616 A | 6/1997 | Liao et al. |
| 5,681,835 A | 10/1997 | Willson |
| 5,712,372 A | 1/1998 | DeGroot et al. |
| 5,958,710 A | 9/1999 | Kuiper et al. |

FOREIGN PATENT DOCUMENTS

| | | |
|---|---|---|
| EP | 0 733 705 A1 | 9/1996 |
| EP | 0 798 378 A2 | 1/1997 |
| WO | WO 97/09348 | 3/1997 |
| WO | WO 99/05171 | 4/1999 |

OTHER PUBLICATIONS

Parker et al., Curr. Opin. Cell. Biol. (1993), vol. 5, pp. 499–504, "Steroid and related receptors".
Greene et al., Science, vol. 231 (1986), pp. 1150–1154, "Sequence and expression of human estrogen receptor complementary DNA".
Koike et al., Nucleic Acids Research, vol. 15, No. 6 (1987), pp. 2499–2513, "Molecular cloning and characterization of rat estrogen receptor cDNA".
Ogawa et al., Biochem. & Biophys. Res. Com., vol. 243 (1998), pp. 122–126, "The complete primary structure of human estrogen receptor beta (hERbeta) . . . ".
Kuiper et al., Proc. Nat'l. Acad. Sci. USA, Vo. 93 (1996), p. 5925–5930, "Cloning of a novel estrogen receptor expressed in rat prostate and ovary".
Lees et al., Nucleic Acids Research, vol. 17, No. 14 (1989), pp. 5477–5488, "Identification of two transactivation domains in the mouse oestrogen receptor".
Tremblay et al., Molec. Endorcin., vol. 11 (1997), pp. 353–365, "Cloning, chromosomal localization, and functional analysis of the murine estrogen receptor beta".
Heikinheimo et al., J. of Assisted Reprod. & Genetics, vol. 12, No. 3 (1995), pp. 198–204, "Animal Investigations: Estrogen and progesterone receptor mRNA are expressed . . . ".
Paech et al., Science, vol. 277 (1997), pp. 1508–1510, "Differential ligand activation of estrogen receptors ERalpha and ERbeta at AP1 sites".
Pennisi, Science, vol. 277 (1997), p. 1439, "Molecular Endocrinology: Differing roles found for estrogen's two receptors".
Enmark et al., Molec. Endorcin., vol. 10, No. 11 (1996), pp. 1293–1307, Orphan nuclear receptors—the first eight years.
Kuiper et al., Abstract from Keystone Symposia on Molecular and Cellular Biology, No. 422, Steroid/Thyroid/Retinoic Acid Gene Family, Lake Tahoe, CA, Mar. 17–23, 1996, "Cloning and characterization of nuclear hormone receptors expressed in rat heart, prostate and colon".
Parker, Trends in Genetics, vol. 12, No. 7 (1996), pp. 277–278, "Nuclear receptor superfamily reunion".
Koeni et al., Proc. Nat'l Acad. Sci. USA, vol. 84 (1987), pp. 5670–5674, "Thyroid hormone receptor binds to a site in the rat growth hormone . . . ".
Ichikawa et al., Proc. Nat'l Acad. Sci. USA, vol. 84 (1987), pp. 3420–3425, "Purification and characterization of rat liver nuclear thyroid hormone receptors".
Underwood et al., Nature, vol. 324 (1986), pp. 425–429, "A thyromimetic that decreases plasma levels without increasing cardiac activity".
Sap et al., Nature, vol. 324 (1986), pp. 635–640, "The c–erb–A protein is a high–affinity receptor for thyroid hormone".

(List continued on next page.)

Primary Examiner—Michael Pak
(74) Attorney, Agent, or Firm—Antonio J. Garcia-Rivas; Mark R. Daniel

(57) ABSTRACT

This invention relates to a novel estrogen receptor and to the polynucleotide sequences encoding this receptor. This invention also relates to methods for identifying ligands which bind to this receptor, to the ligands so identified, and to pharmaceutical compositions comprising such ligands. This invention also relates to pharmaceutical compositions useful for treating or preventing estrogen receptor mediated diseases or conditions, such as abnormal bone resorption, cardiovascular diseases, cancer, or central nervous system disorders.

7 Claims, 2 Drawing Sheets

OTHER PUBLICATIONS

Bishop, Nature, Vo. 321 (1986), pp. opp. 112–113, "Steroid Receptors: Oncogenes as hormone receptors".

Weinberger et al., Nature, vol. 318 (1985), pp. 670–672, "Domain structure of human glucocorticoid receptor and its relationship to the v–erb–A oncogene product".

Jhanwar et al., Somatic Cell and Molec. Genetics, vol. 11 (1985), pp. 99–102, Germ–like chromosomal localization of human c–erb–A oncogene.

West et al., Molec. & Cellular Biol., vol. 7 (1987), pp. 1193–1197, "Interaction of a tissue–specific factor within an essential at growth hormone gene promoter element".

Enmark et al., J. of Clin. Endoc. & Metab., vol. 82 (1997), pp. 4258–4265, "Human estrogen receptor beta–gene structure, chromosomal localization, and expression pattern".

Spurr et al., EMBO Journal, vol. 3 (1984), pp. 159–163, "Chromosomal localisation of the human homologues to the oncogenes erbA and B".

Giguere et al., Cell, vol. 46 (1986), pp. 646–652, Functional domains of the human glucocorticoid receptor.

Vennstrom et al, Cell, vol. 28 (1982), pp. 135–143, "Isolation and characterization of chicken DNA homologous to the two putative oncogenes of avian erythroblastosis virus".

Wight et al., J. of Biol. Chem., vol. 262 (1987), "Discrete positive and negative thyroid hormone–responsive transcription regulatory elements of the rat growth hormone gene".

Torresani et al., Biochem. & Biophys. Res. Comm., vol. 81 (1978), "Partial purification and characterization of nuclear triiodothryronine binding proteins".

Latham et al., J. Biol. Chem., vol. 251 (1976), pp. 7388–7397, "Solubilized nuclear 'receptors' for thyroid hormones".

Silva et al., J. Biol. Chem., vol. 252 (1977), pp. 6799–6805, "Partial purification of triiodothyronine receptor from rat liver nuclei".

Apriletti et al., J. Biol. Chem., vol. 256 (1981), pp. 12094–12101, "Affinity chromatography of thyroid hormone receptors".

Casanova et al., J. of Biol. Chem., vol. 260 (1985), pp. 11744–11748, "5'–Flanking DNA of the rat growth hormone gene mediates regulated expression by thyroid hormone".

Cattini et a., J. Biol. Chem., vol. 261 (1986), pp. 13367–13372, "The human growth hormone gene is negatively regulated by triodothyronine when transferred into rat pituitary tumor cells".

Pascual et al., J. of Biol. Chem., vol. 257 (1982), pp. 9640–9647, "Photoaffinity labeling of thyroid hormone nuclear receptors in intact cells".

Bolger et al., J. Biol. Chem., Vo. 255 (1980), pp. 10271–10278, "Molecular interactions between thyroid hormone analogs and the rat liver nuclear receptor".

Nikodem et al., Proc. Nat'l Acad. Sci. USA, vol. 77 (1980), pp. 7064–7068, "Affinity labeling of rat liver thyroid hormone nuclear receptor".

Zabel et al., Proc. Nat'l Acad. Sci. USA, vol. 81 (1984), pp. 4874–4878, "Cellular homologs of the avian erythroblastosis virus erb–A and erb–B genes are syntenic in mouse . . . ".

Druege et al., Nucleic Acids Research vol. 14 (1986), pp. 9329–9337, "Introduction of estrogen–responsiveness into mammalian cell lines".

Weinberger et al., Nature, vol. 324 (1986), pp. 641–646, "The c–erb gene encodes a thyroid hormone receptor".

Thompson et al., Science, vol. 327 (1987), pp. 1610–1614, "Identification of a novel thyroid hormone receptor expressed in the mammalian central nervous system".

Debuire et al., Science, vol. 224 (1984), "Sequencing the erbA gene of avian erythroblastosis virus reveals a new typeof oncogene".

Casanova et al., J. Biol. Chem., vol. 259 (1984), pp. 12084–12091, "Photoaffinity labeling of thyroid hormone nuclear receptors".

Environ. Heath Perspectives, vol. 104, No. 12 (1996), pp. 1273–1274, "Novel estrogen receptor discovered".

Denton et al., J. Bone & Min. Res. (1997), vol. 12, ASBMR 19th Annual Meeting, Abstract No. 34, p. S111, "Identification of a novel estrogen receptor beta and isoforms expressed in bone and ovary".

Green et al., Nature, vol. 320 (1986), pp. 134–139, "Human oestrogen receptor cDNA: sequence, expression and homology to v–erb–A".

Mosselman et al., FEBS Letters, vol. 392 (1996), pp. 49–53, "ERbeta: identificaton and characterization of a novel human estrogen receptor".

Mangelsdorf et al., Cell., vol. 83 (1995), pp. 835–839, "The nuclear receptor superfamily: overview the second decade".

Shughrue et al., Steroids, vol. 61 (1996), pp. 678–681, "Rapid communication: The distribution of estrogen receptor–beta mRNA in the rat hypothalamus".

Weinberger et al., Cold Spring Harbor Symposium on Quantitative Biology, vol. LI (1986), pp. 759–772, "Human steroid receptors and erbA proto–oncogene products . . . ".

Latham et al., JACC, vol. 9 (1987), pp. 872–876, "Interaction of amiodarone and desethylamiodarone with solubilized nuclear thyroid hormone receptors".

Katzenellenbogen et al., Endocrinology, vol. 138 (1997), pp. 861–862, Editorial: A new actor in the estrogen receptor drama—enter ER–beta.

Angier, The New York Times, Jun. 24, 1997, Col. 1, p. 1, Section C, "New respect for estrogen's influence".

Hitpaβ et al., Cell, vol. 46 (Sep. 1986), pp. 1053–1061, "An estrogen–responsive element derived from the 5' flanking region of the Xenopus Vitellogenin A2 gene functions in transfected human cells".

Chu et al., Molec. & Cellular Endoc., vol. 132 (1997), pp. 195–199, "Identification of a splice variant of the rat estrogen reeptor beta gene".

Peterson et al., Endocrinology, vol. 139 (1998), pp. 1082–1092, "Identification of estrogen receptor beta2, a functional variant of estrogen receptor beta expressed in normal rat tissue".

Damm et al., EMBO Journal, vol. 6, (1987), pp. 375–382, "A single point mutation in erbA restores the erythroid transforming potential of a mutant avian erythroblastosis virus (AEV) defective in both erbA and erbB oncogenes".

MTFVASSCKVFSQLLSQDMDIKNSPSSLNSPSSYNCSQSILPLEHGSIY
IPSSYVDSHHEYPAMTFYSPAVMNYSIPSNVTNLEGGPGRQTTSPNV
LWPTPGHLSPLVVHRQLSHLYAEPQKSPWCEARSLEHTLPVNRETLK
RKVSGNRCASPVTGPGSKRDAHFCAVCSDYASGYHYGVWSCEGCK
AFFKRSIQGHNDYICPATNQCTIDKNRRKSCQACRLRKCYEVGMVK
CGSRRERCGYRLVRRQRSADEQLHCAGKAKRSGGHAPRVRELLLDA
LSPEQLVLTLLEAEPPHVLISRPSAPFTEASMMMSLTKLADKELVHMI
SWAKKIPGFVELSLFDQVRLLESCWMEVLMMGLMWRSIDHPGKLIF
APDLVLDRDEGKCVEGILEIFDMLLATTSRFRELKLQHKEYLCVKAM
ILLNSSMYPLVTATQDADSSRKLAHLLNAVTDALVWVIAKSGISSQQ
QSMRLANLLMLLSHVRHASNKGMEHLLNMKCKNVVPVYDLLLEML
NAHVLRGCKSSITGSECSPAEDSKSKEGSQNPQSQ

FIG.1

```
ATGACCTTTGTAGCCTCTTCTTGCAAGGTGTTTTCTCAGCTGTTATC
TCAAGACATGGATATAAAAAACTCACCATCTAGCCTTAATTCTC
CTTCCTCCTACAACTGCAGTCAATCCATCTTACCCCTGGAGCACG
GCTCCATATACATACCTTCCTCCTATGTAGACAGCCACCATGAAT
ATCCAGCCATGACATTCTATAGCCCTGCTGTGATGAATTACAGCA
TTCCCAGCAATGTCACTAACTTGGAAGGTGGGCCTGGTCGGCAG
ACCACAAGCCCAAATGTGTTGTGGCCAACACCTGGGCACCTTTCT
CCTTTAGTGGTCCATCGCCAGTTATCACATCTGTATGCGGAACCT
CAAAAGAGTCCCTGGTGTGAAGCAAGATCGCTAGAACACACCTT
ACCTGTAAACAGAGAGACACTGAAAAGGAAGGTTAGTGGGAAC
CGTTGCGCCAGCCCTGTTACTGGTCCAGGTTCAAAGAGGGATGC
TCACTTCTGCGCTGTCTGCAGCGATTACGCATCGGGATATCACTA
TGGAGTCTGGTCGTGTGAAGGATGTAAGGCCTTTTTTAAAAGAA
GCATTCAAGGACATAATGATTATATTTGTCCAGCTACAAATCAGT
GTACAATCGATAAAAACCGGCGCAAGAGCTGCCAGGCCTGCCG
ACTTCGGAAGTGTTACGAAGTGGGAATGGTGAAGTGTGGCTCCC
GGAGAGAGAGATGTGGGTACCGCCTTGTGCGGAGACAGAGAAG
TGCCGACGAGCAGCTGCACTGTGCCGGCAAGGCCAAGAGAAGT
GGCGGCCACGCGCCCCGAGTGCGGGAGCTGCTGCTGGACGCCCT
GAGCCCCGAGCAGCTAGTGCTCACCCTCCTGGAGGCTGAGCCGC
CCCATGTGCTGATCAGCCGCCCCAGTGCGCCCTTCACCGAGGCCT
CCATGATGATGTCCCTGACCAAGTTGGCCGACAAGGAGTTGGTA
CACATGATCAGCTGGGCCAAGAAGATTCCCGGCTTTGTGGAGCT
CAGCCTGTTCGACCAAGTGCGGCTCTTGGAGAGCTGTTGGATGG
AGGTGTTAATGATGGGGCTGATGTGGCGCTCAATTGACCACCCC
GGCAAGCTCATCTTTGCTCCAGATCTTGTTCTGGACAGGGATGAG
GGGAAATGCGTAGAAGGAATTCTGGAAATCTTTGACATGCTCCT
GGCAACTACTTCAAGGTTTCGAGAGTTAAAACTCCAACACAAAG
AATATCTCTGTGTCAAGGCCATGATCCTGCTCAATTCCAGTATGT
ACCCTCTGGTCACAGCGACCCAGGATGCTGACAGCAGCCGGAAG
CTGGCTCACTTGCTGAACGCCGTGACCGATGCTTTGGTTTGGGTG
ATTGCCAAGAGCGGCATCTCCTCCCAGCAGCAATCCATGCGCCT
GGCTAACCTCCTGATGCTCCTGTCCCACGTCAGGCATGCGAGTAA
CAAGGGCATGGAACATCTGCTCAACATGAAGTGCAAAAATGTG
GTCCCAGTGTATGACCTGCTGCTGGAGATGCTGAATGCCCACGT
GCTTCGCGGGTGCAAGTCCTCCATCACGGGGTCCGAGTGCAGCCC
GGCAGAGGACAGTAAAAGCAAAGAGGGCTCCCAGAACCCACAGTC
TCAGTGA
```

FIG.2

SEQUENCE LISTING

<160> NUMBER OF SEQ ID NOS: 22

<210> SEQ ID NO 1
<211> LENGTH: 548
<212> TYPE: PRT
<213> ORGANISM: HUMAN

<400> SEQUENCE: 1

```
Met Thr Phe Val Ala Ser Ser Cys Lys Val Phe Ser Gln Leu Leu Ser
 1               5                  10                  15

Gln Asp Met Asp Ile Lys Asn Ser Pro Ser Ser Leu Asn Ser Pro Ser
            20                  25                  30

Ser Tyr Asn Cys Ser Gln Ser Ile Leu Pro Leu Glu His Gly Ser Ile
        35                  40                  45

Tyr Ile Pro Ser Ser Tyr Val Asp Ser His His Glu Tyr Pro Ala Met
    50                  55                  60

Thr Phe Tyr Ser Pro Ala Val Met Asn Tyr Ser Ile Pro Ser Asn Val
65                  70                  75                  80

Thr Asn Leu Glu Gly Gly Pro Gly Arg Gln Thr Thr Ser Pro Asn Val
                85                  90                  95

Leu Trp Pro Thr Pro Gly His Leu Ser Pro Leu Val Val His Arg Gln
            100                 105                 110

Leu Ser His Leu Tyr Ala Glu Pro Gln Lys Ser Pro Trp Cys Glu Ala
        115                 120                 125

Arg Ser Leu Glu His Thr Leu Pro Val Asn Arg Glu Thr Leu Lys Arg
    130                 135                 140

Lys Val Ser Gly Asn Arg Cys Ala Ser Pro Val Thr Gly Pro Gly Ser
145                 150                 155                 160

Lys Arg Asp Ala His Phe Cys Ala Val Cys Ser Asp Tyr Ala Ser Gly
                165                 170                 175

Tyr His Tyr Gly Val Trp Ser Cys Glu Gly Cys Lys Ala Phe Phe Lys
            180                 185                 190

Arg Ser Ile Gln Gly His Asn Asp Tyr Ile Cys Pro Ala Thr Asn Gln
        195                 200                 205

Cys Thr Ile Asp Lys Asn Arg Arg Lys Ser Cys Gln Ala Cys Arg Leu
    210                 215                 220

Arg Lys Cys Tyr Glu Val Gly Met Val Lys Cys Gly Ser Arg Arg Glu
225                 230                 235                 240

Arg Cys Gly Tyr Arg Leu Val Arg Arg Gln Arg Ser Ala Asp Glu Gln
                245                 250                 255

Leu His Cys Ala Gly Lys Ala Lys Arg Ser Gly Gly His Ala Pro Arg
            260                 265                 270

Val Arg Glu Leu Leu Leu Asp Ala Leu Ser Pro Glu Gln Leu Val Leu
        275                 280                 285

Thr Leu Leu Glu Ala Glu Pro Pro His Val Leu Ile Ser Arg Pro Ser
    290                 295                 300

Ala Pro Phe Thr Glu Ala Ser Met Met Met Ser Leu Thr Lys Leu Ala
305                 310                 315                 320

Asp Lys Glu Leu Val His Met Ile Ser Trp Ala Lys Lys Ile Pro Gly
                325                 330                 335

Phe Val Glu Leu Ser Leu Phe Asp Gln Val Arg Leu Leu Glu Ser Cys
            340                 345                 350

Trp Met Glu Val Leu Met Met Gly Leu Met Trp Arg Ser Ile Asp His
```

```
          355                360                365
Pro Gly Lys Leu Ile Phe Ala Pro Asp Leu Val Leu Asp Arg Asp Glu
    370                375                380
Gly Lys Cys Val Glu Gly Ile Leu Glu Ile Phe Asp Met Leu Leu Ala
385                390                395                400
Thr Thr Ser Arg Phe Arg Glu Leu Lys Leu Gln His Lys Glu Tyr Leu
                405                410                415
Cys Val Lys Ala Met Ile Leu Leu Asn Ser Ser Met Tyr Pro Leu Val
            420                425                430
Thr Ala Thr Gln Asp Ala Asp Ser Ser Arg Lys Leu Ala His Leu Leu
        435                440                445
Asn Ala Val Thr Asp Ala Leu Val Trp Val Ile Ala Lys Ser Gly Ile
    450                455                460
Ser Ser Gln Gln Gln Ser Met Arg Leu Ala Asn Leu Leu Met Leu Leu
465                470                475                480
Ser His Val Arg His Ala Ser Asn Lys Gly Met Glu His Leu Leu Asn
                485                490                495
Met Lys Cys Lys Asn Val Val Pro Val Tyr Asp Leu Leu Leu Glu Met
            500                505                510
Leu Asn Ala His Val Leu Arg Gly Cys Lys Ser Ser Ile Thr Gly Ser
        515                520                525
Glu Cys Ser Pro Ala Glu Asp Ser Lys Ser Lys Glu Gly Ser Gln Asn
    530                535                540
Pro Gln Ser Gln
545
```

<210> SEQ ID NO 2
<211> LENGTH: 1647
<212> TYPE: DNA
<213> ORGANISM: HUMAN

<400> SEQUENCE: 2

```
atgacctttg tagcctcttc ttgcaaggtg ttttctcagc tgttatctca agacatggat    60
ataaaaaact caccatctag ccttaattct ccttcctcct acaactgcag tcaatccatc   120
ttacccctgg agcacggctc catatacata ccttcctcct atgtagacag ccaccatgaa   180
tatccagcca tgacattcta tagccctgct gtgatgaatt acagcattcc cagcaatgtc   240
actaacttgg aaggtgggcc tggtcggcag accacaagcc caaatgtgtt gtggccaaca   300
cctgggcacc tttctccttt agtggtccat cgccagttat cacatctgta tgcggaacct   360
caaaagagtc cctggtgtga agcaagatcg ctagaacaca ccttacctgt aaacagagag   420
acactgaaaa ggaaggttag tgggaaccgt tgcgccagcc tgttactgg tccaggttca   480
aagagggatg ctcacttctg cgctgtctgc agcgattacg catcgggata tcactatgga   540
gtctggtcgt gtgaaggatg taaggccttt tttaaaagaa gcattcaagg acataatgat   600
tatatttgtc cagctacaaa tcagtgtaca atcgataaaa accggcgcaa gagctgccag   660
gcctgccgac ttcggaagtg ttacgaagtg ggaatggtga agtgtggctc ccggagagag   720
agatgtgggt accgccttgt gcggagacag agaagtgccg acgagcagct gcactgtgcc   780
ggcaaggcca agagaagtgg cggccacgcg ccccgagtgc gggagctgct gctggacgcc   840
ctgagcccg agcagctagt gctcacccte ctggaggctg agccgcccca tgtgctgatc   900
agccgcccca gtgcgccctt caccgaggcc tccatgatga tgtccctgac caagttggcc   960
gacaaggagt tggtacacat gatcagctgg gccaagaaga ttcccggctt tgtggagctc  1020
```

-continued

```
agcctgttcg accaagtgcg gctcttggag agctgttgga tggaggtgtt aatgatgggg    1080
ctgatgtggc gctcaattga ccaccccggc aagctcatct ttgctccaga tcttgttctg    1140
gacagggatg aggggaaatg cgtagaagga attctggaaa tctttgacat gctcctggca    1200
actacttcaa ggtttcgaga gttaaaactc caacacaaag aatatctctg tgtcaaggcc    1260
atgatcctgc tcaattccag tatgtaccct ctggtcacag cgacccagga tgctgacagc    1320
agccggaagc tggctcactt gctgaacgcc gtgaccgatg ctttggtttg ggtgattgcc    1380
aagagcggca tctcctccca gcagcaatcc atgcgcctgg ctaacctcct gatgctcctg    1440
tcccacgtca ggcatgcgag taacaagggc atggaacatc tgctcaacat gaagtgcaaa    1500
aatgtggtcc cagtgtatga cctgctgctg gagatgctga atgcccacgt gcttcgcggg    1560
tgcaagtcct ccatcacggg gtccgagtgc agcccggcag aggacagtaa aagcaaagag    1620
ggctcccaga acccacagtc tcagtga                                        1647

<210> SEQ ID NO 3
<211> LENGTH: 25
<212> TYPE: DNA
<213> ORGANISM: HUMAN

<400> SEQUENCE: 3
ggagaaaggt gcccaggtgt tggcc                                            25

<210> SEQ ID NO 4
<211> LENGTH: 23
<212> TYPE: DNA
<213> ORGANISM: HUMAN

<400> SEQUENCE: 4
gtggtctgcc gaccaggccc acc                                              23

<210> SEQ ID NO 5
<211> LENGTH: 23
<212> TYPE: DNA
<213> ORGANISM: HUMAN

<400> SEQUENCE: 5
ggtgttggcc acaacacatt tgg                                              23

<210> SEQ ID NO 6
<211> LENGTH: 22
<212> TYPE: DNA
<213> ORGANISM: HUMAN

<400> SEQUENCE: 6
gtaatacgac tcactatagg gc                                               22

<210> SEQ ID NO 7
<211> LENGTH: 23
<212> TYPE: DNA
<213> ORGANISM: HUMAN

<400> SEQUENCE: 7
gttagtgaca ttgctgggaa tgc                                              23

<210> SEQ ID NO 8
<211> LENGTH: 23
<212> TYPE: DNA
<213> ORGANISM: HUMAN
```

-continued

<400> SEQUENCE: 8
gatcagaggc ttcagcgaaa cag                                    23

<210> SEQ ID NO 9
<211> LENGTH: 24
<212> TYPE: DNA
<213> ORGANISM: HUMAN

<400> SEQUENCE: 9
gaacgcgtgg attagtgact agcc                                   24

<210> SEQ ID NO 10
<211> LENGTH: 23
<212> TYPE: DNA
<213> ORGANISM: HUMAN

<400> SEQUENCE: 10
ggaggaagga gaattaaggc tag                                    23

<210> SEQ ID NO 11
<211> LENGTH: 23
<212> TYPE: DNA
<213> ORGANISM: HUMAN

<400> SEQUENCE: 11
gagataacag ctgagaaaac acc                                    23

<210> SEQ ID NO 12
<211> LENGTH: 44
<212> TYPE: DNA
<213> ORGANISM: HUMAN

<400> SEQUENCE: 12
gtgatgaatt acagcattcc cagcaatgtc actaacttgg aagg             44

<210> SEQ ID NO 13
<211> LENGTH: 41
<212> TYPE: DNA
<213> ORGANISM: HUMAN

<400> SEQUENCE: 13
atggcccaag cttgggttcc agttcacctc agggccaggc g                41

<210> SEQ ID NO 14
<211> LENGTH: 23
<212> TYPE: DNA
<213> ORGANISM: HUMAN

<400> SEQUENCE: 14
cttggaaggt gggcctggtc ggc                                    23

<210> SEQ ID NO 15
<211> LENGTH: 25
<212> TYPE: DNA
<213> ORGANISM: HUMAN

<400> SEQUENCE: 15
ggagaaaggt gcccaggtgt tggcc                                  25

<210> SEQ ID NO 16
<211> LENGTH: 24
<212> TYPE: DNA
<213> ORGANISM: HUMAN

-continued

```
<400> SEQUENCE: 16
ccgttgcgcc agccctgtta ctgg                                              24

<210> SEQ ID NO 17
<211> LENGTH: 23
<212> TYPE: DNA
<213> ORGANISM: HUMAN

<400> SEQUENCE: 17
cgcaagagct gccaggcctg ccg                                               23

<210> SEQ ID NO 18
<211> LENGTH: 23
<212> TYPE: DNA
<213> ORGANISM: HUMAN

<400> SEQUENCE: 18
ccccgagcag ctagtgctca ccc                                               23

<210> SEQ ID NO 19
<211> LENGTH: 23
<212> TYPE: DNA
<213> ORGANISM: HUMAN

<400> SEQUENCE: 19
cttggagagc tgttggatgg agg                                               23

<210> SEQ ID NO 20
<211> LENGTH: 22
<212> TYPE: DNA
<213> ORGANISM: HUMAN

<400> SEQUENCE: 20
ctctgtgtca aggccatgat cc                                                22

<210> SEQ ID NO 21
<211> LENGTH: 24
<212> TYPE: DNA
<213> ORGANISM: HUMAN

<400> SEQUENCE: 21
cgtcaggcat gcgagtaaca aggg                                              24

<210> SEQ ID NO 22
<211> LENGTH: 24
<212> TYPE: DNA
<213> ORGANISM: HUMAN

<400> SEQUENCE: 22
gcaagtcctc catcacgggg tccg                                              24
```

POLYNUCLEOTIDE ENCODING ESTROGEN RECEPTOR

CROSS-REFERENCE TO RELATED APPLICATIONS

This application is a divisional of U.S. application Ser. No. 09/139,617, filed Aug. 25, 1998 now U.S. Pat. No. 6,222,015, and claims priority to U.S. Provisional Provisional Patent Applications No. 60/060,520, filed Sep. 30, 1997, and Ser. No. 60/058,271, filed Sep. 8, 1997, both now abandoned.

FIELD OF THE INVENTION

This invention relates to a novel estrogen receptor and to the polynucleotide sequences encoding this receptor. This invention also relates to methods for identifying ligands which bind to this receptor, to the ligands so identified, and to pharmaceutical compositions comprising such ligands. This invention also relates to pharmaceutical compositions useful for treating or preventing estrogen receptor mediated diseases or conditions.

BACKGROUND OF THE INVENTION

Nuclear receptors are a large class of proteins that are responsible for the regulation of complex cellular events including cell differentiation, homeostasis, the growth and functioning of various organs and tissues, and transcription. It is believed that nuclear receptors function by transducing extracellular chemical signals from hormones into a transcriptional response.

Estrogen receptors are a subclass of the larger nuclear receptor class. The estrogen receptors are proteins that are responsive to estrogen and estrogen-like molecules. Estrogen receptors are believed to play an important role in the mammalian endocrine system, the reproductive organs, breast tissue, bone tissue, and the vascular system, and are believed to be involved in the development and progression of various disease states such as abnormal bone resorption, cardiovascular disease, cancer, and central nervous system disorders. It is believed that various disease states and conditions can be treated or prevented by the development of appropriate ligands, i.e. drugs, for modifying the activity of estrogen receptors. Consequently there is a need to identify estrogen receptors and their mode of action and to also identify ligands for modifying the action of these receptors.

At least two distinct types of estrogen receptors have been reported. An estrogen receptor having 595 amino acids is disclosed in Green, S. et al., *Nature*, 320, pp. 134–139 (1986) and Greene, G. L. et al., *Science*, 231, pp. 1150–1154 (1986), both of which are incorporated by reference herein in their entirety. These references also disclose the corresponding DNA sequences for the receptor.

The other reported type of estrogen receptor has been disclosed by two research groups and has been designated "β" (beta). One research group discloses a 485 amino acid β receptor that is obtained from rat, human, and mouse sources, as well as the corresponding DNA sequences. See PCT application No. WO 97/09348, to Kuiper, G. G. J. M. et al., published Mar. 13, 1997, which is incorporated by reference herein in its entirety. The second research group discloses a similar estrogen receptor containing 483 amino acids. The corresponding DNA sequence is also disclosed. See Mosselman, S. et al., ERβ: identification and characterization of a novel human estrogen receptor, FEBS Letters, 392, pp. 49–53 (1996), which is incorporated by reference herein in its entirety.

In the present invention, a novel estrogen receptor having 548 amino acid units, and that is distinct from the disclosed 595 amino acid, 485 amino acid, and 483 amino acid estrogen receptors, has been identified and isolated from human tissue. It is believed that this novel estrogen receptor plays a key role in mammalian physiology. This novel estrogen receptor is an important research tool for identifying and designing ligands for use in pharmaceutical compositions for treating and/or preventing a wide range of estrogen receptor mediated diseases or conditions.

It is therefore an object of the present invention to provide a novel isolated estrogen receptor.

It is another object of the present invention to provide the amino acid sequence of a novel estrogen receptor.

It is another object of the present invention to provide the polynucleotide sequence encoding a novel estrogen receptor.

It is another object of the present invention to provide methods for isolating a novel estrogen receptor.

It is another object of the present invention to provide ligands capable of binding to a novel estrogen receptor.

It is another object of the present invention to provide pharmaceutical compositions comprising ligands capable of binding to a novel estrogen receptor.

It is another object of the present invention to provide methods for treating and/or preventing estrogen receptor mediated diseases or conditions.

These and other objects will become readily apparent from the detailed description which follows.

SUMMARY OF THE INVENTION

The present invention relates to an isolated estrogen receptor comprising the amino acid sequence of FIG. 1 (which also corresponds to SEQ ID NO: 1).

In further embodiments, the present invention relates to an isolated estrogen receptor having an amino acid sequence that is substantially similar to the amino acid sequence of FIG. 1 (SEQ ID NO: 1) werein the estrogen receptor comprises at least 531 amino acids.

In further embodiments, the present invention relates to an isolated estrogen receptor comprising at least 531 amino acids and having substantially the same ligand binding properties or substantially the same DNA binding properties as the estrogen receptor of FIG. 1 (SEQ ID NO: 1).

In further embodiments, the present invention relates to an isolated estrogen receptor that is derived from mammalian cells, preferably human cells.

In further embodiments, the present invention relates to an isolated polynucleotide encoding the estrogen receptor having the amino acid sequence of FIG. 1 (SEQ ID NO: 1).

In further embodiments, the present invention relates to an isolated polynucleotide which is a DNA, a cDNA, or an RNA.

In further embodiments, the present invention relates to an isolated polynucleotide which hydridizes to and is complementary to the polynucleotide encodingl the estrogen receptor having the amino acid sequence of FIG. 1 (SEQ ID NO: 1).

In further embodiments, the present invention relates to an isolated polynucleotide comprising a polynucleotide encoding a mature polypeptide encoded by the estrogen receptor polynucleotide contained in an ATCC Deposit selected from the group consisting of ATCC Deposit No. 209238, ATCC Deposit No. 209239, and ATCC Deposit No. 209240.

In further embodiments, the present invention relates to an isolated polynucleotide comprising the nucleotide sequence of FIG. 2 (which also corresponds to SEQ ID NO: 2).

In further embodiments, the present invention relates to an isolated polynucleotidwhich hybyridizes to and is complementary to the polynucleotide of FIG. 2 (SEQ ID NO: 2), wherein said polynucleotide comprises at least 1593 nucleotides.

In further embodiments, the present invention relates to a vector containing the DNA.

In further embodiments, the present invention relates to a host cell transformed or transfected with the vector of the present invention.

In further embodiments, the present invention relates to a method for producing an estrogen receptor of the present invention.

In further embodiments, the present invention relates to a method for determining whether a ligand can bind to the estrogen receptor of the present invention.

In further embodiments, the present invention relates to a ligand detected by the methods of the present invention.

In further embodiments, the present invention relates to a pharmaceutical composition comprising a ligand of the present invention.

In further embodiments, the present invention relates to a method for treating or preventing an estrogen receptor mediated disease or condition by administering an effective amount of a pharmaceutical composition of the present invention.

The deposits referred to herein will be maintained under the Budapest Treaty on the International Recognition of the Deposit of Microorganisms for the purposes of Patent Procedure. These deposits are provided merely as a convenience and are not an admission that a deposit is required under 35 USC §112. The sequence of the polynucleotides contained in the deposited materials, as well as the amino acid sequence of the polypeptides encoded thereby, are incorporated herein by reference in their entirety and are controlling in the event of any conflict with the description of the sequences herein. A license may be required to make, use or sell the deposited materials, and no such license is hereby granted.

All percentages and ratios used herein, unless otherwise indicated, are by weight. The invention hereof can comprise, consist of, or consist essentially of the essential as well as optional ingredients, components, and methods described herein.

BRIEF DESCRIPTION OF THE FIGURES

FIG. 1 shows the amino acid sequence of the estrogen receptor (SEQ ID NO: 1), i.e. the polypeptide, of the present invention.

FIG. 2 shows the nucleotide sequence, i.e. the cDNA polynucleotide (SEQ ID NO: 2), encoding the estrogen receptor of the present invention. This sequence includes the translation termination codon "TGA".

DESCRIPTION OF THE INVENTION

In accordance with one aspect of the present invention, there is provided a polypeptide, namely an estrogen receptor, which has the deduced amino acid sequence of FIG. 1 (SEQ ID NO: 1) or which has the amino acid sequence encoded by the cDNA of the clone deposited as ATCC Deposit No. 209238 on Sep. 8, 1997, by the genomic DNA of the clone deposited as ATCC Deposit No. 209239 on Sep. 8, 1997, or by the genomic DNA of the clone deposited as ATCC Deposit No. 209240 on Sep. 8, 1997. The present invention also relates to fragments, analogs and derivatives of such an estrogen receptor.

The terms "fragments", "derivatives", and "analogs" when referring to the estrogen receptor of FIG. 1 (SEQ ID NO: 1) or that encoded by the deposited DNA, means a polypeptide which retains essentially the same biological function or activity as such estrogen receptor. Thus, an analog includes a proprotein which can be activated by cleavage of the proprotein portion to produce an active mature estrogen receptor.

The estrogen receptor of the present invention can be a recombinant polypeptide, a natural plypeptide, or a synthetic polypeptide of the sequence of FIG. 1 (SEQ ID NO: 1), or that encoded by the deposited DNA. Also contemplated within the scope of the present invention are splice variants of the receptor of FIG. 1 (SEQ ID NO: 1), or encoded by the deposited DNA.

The fragments, derivatives, or analogs of the estrogen receptor of FIG. 1 (SEQ ID NO: 1) or that encoded by the deposited DNA can be (i) one in which one or more of the amino acid residues are substituted with a conserved or non-conserved amino acid residue (preferably a conserved amino acid residue) and such substituted amino acid residue can be one that is or is not encoded by the genetic code, or (ii) one in which one or more of the amino acid residues includes a substituent group, or (iii) one in which the mature estrogen receptor is fused with another compound, such as a compound to increase the half-life of the estrogen receptor (for example, polyethylene glycol), or (iv) one in which the additional amino acids are fused to the mature estrogen receptor, such as a leader or secretory sequence or a sequence which is employed for purification of the mature estrogen receptor or a proprotein sequence. Such fragments, derivatives and analogs are deemed to be within the scope of those skilled in the art from the teachings herein.

The present invention also encompasses estrogen receptors which have substantially the same amino acid sequence as the estrogen receptor of FIG. 1 (SEQ ID NO: 1). In further embodiments of the present invention, the isolated estrogen receptor comprises at least 531 amino acid units and is at least about 75% identical with the sequence shown in FIG. 1 (SEQ ID NO: 1). In even further embodiments of the present invention, the isolated estrogen receptor comprises at least 531 amino acid units and is at least about 90% identical with the sequence shown in FIG. 1 (SEQ ID NO: 1). In even further embodiments of the present invention, the isolated estrogen receptor comprises at least 531 amino acid units and is at least about 95% identical with the sequence shown in FIG. 1 (SEQ ID NO: 1). In even further embodiments of the present invention, the isolated estrogen receptor comprises at least 531 amino acid units and.is,at least about 99% identical with the sequence shown in FIG. (SEQ ID NO: 1).

The present invention also encompasses estrogen receptors comprising at least 531 amino acids and having substantially the same ligand binding properties or substantially the same DNA binding properties as that of the estrogen receptor of FIG. 1 (SEQ ID NO: 1). In other words, the respective ligand binding or DNA binding domains of the receptors have at least about 75%, homology, preferably about 90% homology, more preferably about 95% homology, and most preferably about 99% homology to each of the respective ligand binding and DNA binding domains in the receptor of FIG. 1 (SEQ ID NO: 1).

In accordance with another aspect of the present invention, there is provided an isolated nucleic acid, i.e. the polynucleotide, which encodes for the mature estrogen receptor having the deduced amino acid sequence of FIG. 1 (SEQ ID NO: 1), or for the mature estrogen receptor encoded by the DNA of the deposited clones.

A polynucleotide encoding an estrogen receptor of the present invention can be obtained by performing polymerase chain reactions (PCR) on human testis cDNA and subcloning into a vector in JM109 E. coli. Alternatively, the polynucleotide can be obtained by screening a human genomic DNA library derived from human testis.

The polynucleotide of the present invention can be in the form of RNA or in the form of DNA, which DNA includes cDNA, genomic DNA, and synthetic DNA. The DNA can be double-stranded or single-stranded, and if single stranded can be the coding strand or non-coding (anti-sense) strand. The coding sequence which encodes the mature estrogen receptor can be identical to the coding sequence shown in FIG. 2 or that of the deposited clones or can be a different coding sequence, which coding sequence, as a result of redundancy or degeneracy of the genetic code, encodes the same, mature estrogen receptors as the DNA of FIG. 2 (SEQ ID NO: 2) or the deposited DNA.

The polynucleotide which encodes for the mature estrogen receptor of FIG. 1 (SEQ ID NO: 1) or for the mature polypeptide encoded by the deposited DNA can include: only the coding sequence for the mature polypeptide; the coding sequence for the mature polypeptide and additional coding sequence such as a leader or secretory sequence or a proprotein sequence; or the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 (SEQ ID NO: 1) or the polypeptide encoded by the DNA of the deposited clones. The variant of the polynucleotide can be a naturally occurring allelic variant of the polynucleotide. The present invention also relates to polynucleotide probes constructed from the polynucleotide sequence of FIG. 2 (SEQ ID NO: 2) or a segment of the sequence of FIG. 2 amplified by the PCR method, which can be utilized to screen a cDNA library to deduce the estrogen receptor of the present invention.

Thus, the present invention includes polynucleotides encoding the same mature estrogen receptor as shown in FIG. 1 (SEQ ID NO: 1) or the same mature polypeptide encoded by the DNA of the deposited clones, as well as variants of such polynucleotides which variants encode for fragments, derivatives or analogs of the polypeptide of FIG. 2 (SEQ ID NO: 2) or the polypeptide encoded by the DNA of the deposited clones. Such nucleotide variants include deletion variants, substitution variants and addition or insertion variants.

As hereinabove indicated, the polynucleotide can have a coding sequence which is a naturally occurring allelic variant of the coding sequence shown in FIG. 2 (SEQ ID NO: 2) of the coding sequence of the deposited clones. As known in the art, an allelic variant is an alternate form of a polynucleotide sequence which can have a substitution, deletion or addition of one or more nucleotides, which does not substantially alter the function of the encoded polypeptide.

The present invention further relates to polynucleotides which hybridize to the polynucleotides encoding the estrogen receptor having the amino acid sequence of FIG. 1 (SEQ ID NO: 1). The present invention relates to an isolated polynucleotide which hybridizes to and is at least about 75% complementary to the polynucleotide encoding the estrogen receptor having the amino acid sequence of FIG. (SEQ ID NO: 1). The present invention relates to an isolated polynucleotide which hybridizes to and is at least about 90% complementary to the polynucleotide encoding the estrogen receptor having the amino acid sequence of FIG. 1. The present invention relates to an isolated polynucleotide which hybridizes to and is at least about 95% complementary to the polynucleotide encoding the estrogen receptor having the amino acid sequence of FIG The present invention relates to an isolated polynucleotide which hybridizes to and is at least about 99% complementary to the polynucleotide encoding the estrogen receptor having the amino acid sequence of FIG. 1 (SEQ ID NO: 1).

The present invention relates to an isolated polynucleotide comprising at least 1593 nucleotides. The present invention relates to an isolated polynucleotide comprising at least 1593 nucleotides which hybridizes to and is at least about 75% complementary to the polynucleotide of FIG. 2. The present invention relates to an isolated polynucleotide comprising at least 1593 nucleotides which hybridizes to and is at least about 90% complementary to the polynucleotide of FIG. 2. The present invention relates to an isolated polynucleotide comprising at least 1593 nucleotides which hybridizes to and is at least about 95% complementary to the polynucleotide of FIG. 2. The present invention relates to an isolated polynucleotide which hybridizes to and is at least about 99% complementary to the polynucleotide of FIG. 2 (SEQ ID NO: 2).

The polynucleotides which hybridize to the hereinabove described polynucleotides encode estrogen receptors which retain substantially the same biological function or activity as the mature estrogen receptors encoded by the cDNA of FIG. 2 (SEQ ID NO: 2) or the deposited DNA. Hybridization is described in U.S. Pat. No. 5,501,969, to Hastings et al., issued Mar. 26, 1996, which is incorporated by reference herein in its entirety.

The polypeptides and polynucleotides of the present invention are preferably provided in an isolated form, and preferably are purified to homogeneity.

The term "isolated" means that the material is removed from its original environment (e.g., the natural environment if it is naturally-occuring). For example, a naturally-occuring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that such vector or composition is not part of its natural environment.

The present invention also relates to vectors which include polynucleotides of the present invention, host cells which are genetically engineered with vectors of the invention and the production of estrogen receptors of the invention by recombinant techniques.

Host cells are genetically engineered (transduced or transformed or transfected) with the vectors of this invention which can be, for example, a cloning vector or an expression vector. The vector can be, for example in the form of a plasmid, a viral particle, a phage, etc. The engineered host cells can be cultured in conventional nutrient media modified for activating promoters, selecting transformants or amplifying the estrogen receptor genes. The culture conditions, such as temperature, pH and the like, are those previously used with the host cell selected for expression, and will be apparent to the ordinarily skilled artisan.

The polynucleotide of the present invention can be employed for producing a polypeptide by recombinant techniques. Thus, for example, the polynucleotide sequence can be included in any one of a variety of expression vehicles, in particular vectors or plasmids for expressing an estrogen receptor. Such vectors include chromosomal, nonchromosomal and synthetic DNA sequences, e.g., derivatives of SV40: bacterial plasmids; phage DNA; yeast plasmids; vectors derived from combinations of plasmids and phage DNA, viral DNA such as vaccinia, adenovirus, fowl, pox virus, and pseudorabies. However, any other plasmid or vector can be used as long as it is replicable and viable in the host.

As hereinabove indicated the appropriate DNA sequence can be inserted into the vector by a variety of procedures. In general, the DNA sequence is inserted into appropriate restriction endonuclease sites by procedures known in the art. Such procedures and others are deemed to be within the scope of those skilled in the art.

The present invention also includes recombinant constructs comprising one or more of the sequences as broadly defined herein. The constructs comprise a vector, such as a plasmid or viral vector, into which a sequence of the invention has been inserted, in a forward or reverse orientation. Large numbers of suitable vectors and promoters are known to those of skill in the art, and are commercially available.

In a further embodiment, the present invention relates to host cells containing the above-described construct. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., *Basic Methods in Molecular Biology*, 1986, which is incorporated by reference herein in its entirety).

The constructs in host cells can be used in a conventional manner to produce the gene product encoded by the recombinant sequence. Alternatively, the estrogen receptors of the present invention can be synthetically produced by conventional peptide synthesizers.

Mature estrogen receptors can be expressed in mammalian cells, yeast, bacteria, or other cells under the control of appropriate promoters.

Cell-free translation systems can also be employed to produce such estrogen receptors using RNAs derived from the DNA constructs of the present invention. Appropriate cloning and expression vectors for use with prokaryotic and eukaryotic hosts are described by Sambrook et al., *Molecular Cloning: A Laboratory Manual*, Second Edition (Cold Spring Harbor, N.Y., 1989), which is incorporated by reference herein in its entirety.

The estrogen receptors of the present invention can be naturally purified products expressed from a high expressing cell line, or a product of chemical synthetic procedures, or produced by recombinant techniques from a prokaryotic or eukaryotic host (for example, by bacterial, yeast, higher plant, insect and mammalian cells in culture). Alternatively, a baculovirus/insect cell expression system can also be employed.

The estrogen receptors, their fragments or other derivatives or analogs thereof, or cells expressing them can be used as an immunogen to produce antibodies thereto. These antibodies can be, for example, polyclonal or monoclonal antibodies. The present invention also includes chimeric, single chain and humanized antibodies, as well as Fab fragments, or the product of a Fab expression library. Various procedures known in the art can be used for the production of such antibodies and fragments.

The present invention is also directed to ligands, i.e. drugs, of the estrogen receptors herein. The term "ligand" as used herein means any molecule which binds to the estrogen receptor of the present invention. These ligands can have either agonist, partial agonist, antagonist, partial antagonist, inverse agonist, or mixtures of these properties. Thus, for example, a ligand that binds to an estrogen receptor of the present invention might modify, inhibit, or eliminate its function. In this way, the ligand can be used to treat or prevent a disease in which the estrogen receptor is involved. The ligands contemplated herein are those that have selectivity to specifically activate or inhibit genes that are normally regulated by the estrogen receptors of the present invention.

The present invention also relates to methods for determining whether a ligand not known to be capable of binding to a human estrogen receptor can bind to a human estrogen receptor. These methods comprise contacting a mammalian cell comprising an isolated DNA molecule encoding a human estrogen receptor with the ligand under conditions permitting binding of ligands known to bind to an estrogen receptor, detecting the presence of any of the ligand bound to a human estrogen receptor, and thereby determining whether the ligand binds to a human estrogen receptor. In these methods, the mammalian cell is actually expressing the isolated DNA molecules. The general methodology for conducting such a method is well known to those of ordinary skill in the art. See EP 787,797, to Weinshank et al., published Jul. 6, 1997, which is incorporated by reference herein in its entirety. Alternatively, RNA that ultimately encodes for the estrogen receptor could be injected into, for example Xenopus oocytes, and expressed, and used in analogous assay experiments.

The present invention also relates to pharmaceutical compositions comprising the ligands of the present invention. Such compositions comprise a pharmaceutically effective amount of the ligand. The term "pharmaceutically effective amount", as used herein, means that amount of the ligand that will elicit the desired therapeutic effect or response when administered in accordance with the desired treatment regimen. The ligand is typically administered in admixture with suitable pharmaceutical diluents, excipients, or carriers, collectively referred to herein as "carrier materials", suitably selected with respect to the mode of administration, i.e. oral, I.V., nasal, parenteral, ocular, etc. A wide variety of product and dosage forms well known to one of ordinary skill in the art can be used to administer these ligands.

The present invention also relates to methods for treating and/or preventing estrogen receptor mediated diseases or conditions. By "estrogen receptor mediated diseases or conditions" is meant a physiological or pathological state in which an estrogen receptor is involved. Nonlimiting examples of estrogen receptor mediated diseases or conditions include those of the endocrine system, the reproductive organs, breast tissue, bone tissue, and the vascular system, especially those diseases that become more prevelant in aging males and females. More specifically, such diseases and conditions include those selected from the group consisting of abnormal bone resorption, cardiovascular disease, cancer, metabolic disorders, and central nervous system disorders. Even more specifically, such diseases and conditions include those selected from the group consisting of osteoporosis, breast cancer, uterine cancer, ovarian cancer, prostate cancer, diabetes, and Alzheimer's disease.

EXAMPLES

The following examples further describe and demonstrate embodiments within the scope of the present invention. The examples are given solely for the purpose of illustration and are not to be construed as limitations of the present invention as many variations thereof are possible without departing from the spirit and scope of the invention.

Example 1

Cloning and Sequencing of cDNA Clones of a Human Estrogen Receptor Gene

The 5' rapid amplification of cDNA ends (RACE) product was identified by performing two rounds of polymerase chain reactions (PCR) on human testis Marathon-Ready cDNA (Clontech product #7414-1) using Vent Polymerase (New England Biolabs product #254S). The first round of PCR was performed using the oligonucleotide, GGAGAAAGGTGCCCAGGTGTTGGCC (SEQ ID NO: 3), in the 5' coding region of human estrogen receptor beta (GenBank sequence number X99101) and the Clontech AP1 primer, according to the manufacturer's instructions. The second round of PCR was performed using either of two different nested primers having the sequences GTGGTCT-GCCGACCAGGCCCACC (SEQ ID NO: 4) or GGTGT-TGGCCACAACACATTTGG (SEQ ID NO: 5), corresponding to the 5' end of a human estrogen receptor beta clone (GenBank sequence number X99101), and the Clontech AP2 primer, according to the manufacturer's instructions. The PCR product was subcloned into the PCRAmp-Script vector (Stratagene product # 211188) in JM109 E. coli. This clone was sequenced on both strands by cycle sequencing (Pharmacia product #27-1694-01), according to the manufacturer's instructions using primers corresponding to the vector sequence having the following sequence GTAATACGACTCACTATAGGGC (SEQ ID NO: 6) as well as a primer in the 5' end of the human estrogen receptor beta receptor gene having the following sequence GTTAGT-GACATTGCTGGGAATGC (SEQ ID NO: 7). Further sequencing was performed with four additional primers having the following sequences: GATCAGAGGCT-TCAGCGAAACAG (SEQ ID NO: 8), GAACGCGTG-GATTAGTGACTAGCC (SEQ ID NO: 9), GGAGGAAG-GAGAATTAAGGCTAG (SEQ ID NO: 10), and GAGATAACAGCTGAGAAAACACC (SEQ ID NO: 11). These four primers were derived from the initial sequence analysis. Sequence alignments and analysis of the nucleotide and protein sequences were carried out using MacVector and AssemblyLign programs (Oxford Molecular Group) as well as the GCG Sequence Analysis Software Package (Madison, Wis.: pileup).

Example 2

Cloning and Sequencing of Genomic DNA Clones of a Human Estrogen Receptor Gene

To obtain a probe for use in the screening of a human genomic DNA library, cDNA was first generated from human testis mRNA (Clontech product #6535-1) using an oligo-dT primer and MMLV Reverse Transcriptase (Stratagene product #200420) according to the manufacturer's instructions. The cDNA was amplified by PCR using Boehringer Mannheim's Expand High Fidelity PCR System (product #1732 641) and two primers having the following sequences: GTGATGAATTACAGCATTCCCAGCAAT-GTCACTAACTTGGAAGG (SEQ ID NO: 12) and ATGGC CCAAGCTTGGGTTCCAGTTCACCTCAGGGC CAG-GCG (SEQ ID NO: 13). The PCR product was cloned into the TGEM vector (Promega product #A3600) in JM109 E. coli. The product was sequenced on one strand with a Pharmacia cycle sequencing kit (product #27-1694-01) according to the manufacturer's instructions using nine primers having the following sequences: CTTGGAAG-GTGGGCCTGGTCGGC (SEQ ID NO: 14), GGAGAAAG-GTGCCCAGGTGTTGGCC (SEQ ID NO: 15, which is identical to SEQ ID NO: 3), CCGTTGCGCCAGCCCTGT-TACTGG (SEQ ID NO: 16), CGCAAGAGCTGCCAGGC-CTGCCG (SEQ ID NO: 17), CCCCGAGCAGCTAGT-GCTCACCC (SEQ ID NO: 18), CTTGGAGAGCTGTTGGATGGAGG (SEQ ID NO: 19), CTCTGTGTCAAGGCCATGATCC (SEQ ID NO: 20), CGTCAGGCATGCGAGTAACAAGGG (SEQ ID NO: 21), and GCAAGTCCTCCATCACGGGGTCCG (SEQ ID NO: 22), corresponding to the published DNA sequence (Mosselman, S. et al., ERA: identification and characterization of a novel human estrogen receptor, *FEBS Letters*, 392, pp. 49–53 [1996]). Sequence alignments and analysis of the nucleotide and protein sequences were carried out using MacVector and AssemblyLign programs (Oxford Molecular Group) as well as the GCG Sequence Analysis Software Package (Madison, Wis.: pileup).

The cDNA clone obtained was digested with the restriction enzymes NcoI and KpnI to obtain an approximately 500 base pair fragment corresponding to the 5' end of the human estrogen receptor beta cDNA (GenBank sequence number X99101). This fragment was labeled with P-32 and used to screen a human genomic DNA library (Stratagene product #946206) as per the manufacturer's instructions. One million bacteriophage plaques were screened and seventeen potential hybridizing phages were chosen. These phages were reamplified and screened using a slightly smaller probe (i.e an approximately 300 base pair fragment generated by digesting the human ERbeta clone with NcoI and PstI). Two positive phages were plaque purified and used for the production of DNA. The phages were digested with NotI and BaniHI to generate smaller fragments encoding most of the phage DNA and these were subcloned into pBluescript (Stratagene; GenBank #52324). There were two fragments from one phage of approximately 8.5 and 6 kb and two fragments from the other phage of approximately 7.7 and 6.3 kb. The genomic subclones of 8.5 and 7.7 kb were sequenced on both strands with a Pharmacia cycle sequencing kit (product #27-1694-01) according to the manufacturer's instructions using primers derived from the 5'RACE product sequencing (EXAMPLE 1). Sequence alignments and analysis of the nucleotide and protein sequences were carried out using MacVector and AssemblyLign programs (Oxford Molecular Group) as well as the GCG Sequence Analysis Software Package (Madison, Wis.: pileup).

What is claimed is:

1. An isolated polynucleotide encoding the estrogen receptor having the amino acid sequence of SEQ ID NO:1.
2. An isolated polynucleotide comprising the nucleotide sequence of SEQ ID NO:2.
3. The polynucleotide of claim 1 wherein the polynucleotide is DNA.
4. The DNA of claim 3 wherein the DNA is a cDNA.
5. A isolated vector containing the DNA of claim 3.
6. A isolated host cell transformed or transfected with the vector of claim 5.
7. A method for producing an estrogen receptor comprising:

expressing from the host cell of claim 6 the estrogen receptor encoded by said DNA.

* * * * *